United States Patent
Gehrke et al.

(10) Patent No.: US 9,181,149 B2
(45) Date of Patent: Nov. 10, 2015

(54) REGENERATION OF CATALYSTS FOR DEHYDRATING ALKANES

(75) Inventors: Helmut Gehrke, Bergkamen (DE); Max Heinritz-Adrian, Muenster (DE); Muhammad Iqbal Mian, Dortmund (DE); Oliver Noll, Castrop-Rauxel (DE); Rolf Schwass, Neubeckum (DE); Sascha Wenzel, Bochum (DE)

(73) Assignee: THYSSENKRUPP INDUSTRIAL SOLUTIONS AG, Essen (DE)

( * ) Notice: Subject to any disclaimer, the term of this patent is extended or adjusted under 35 U.S.C. 154(b) by 854 days.

(21) Appl. No.: 12/452,933

(22) PCT Filed: Jul. 24, 2008

(86) PCT No.: PCT/EP2008/006059
§ 371 (c)(1),
(2), (4) Date: May 19, 2010

(87) PCT Pub. No.: WO2009/018924
PCT Pub. Date: Feb. 12, 2009

(65) Prior Publication Data
US 2010/0234660 A1 Sep. 16, 2010

(30) Foreign Application Priority Data
Aug. 3, 2007 (DE) .......................... 10 2007 036 750

(51) Int. Cl.
*C07C 5/333* (2006.01)
*B01J 38/06* (2006.01)
*B01J 38/16* (2006.01)
B01J 23/24 (2006.01)
B01J 23/40 (2006.01)

(52) U.S. Cl.
CPC ............... *C07C 5/3335* (2013.01); *B01J 38/06* (2013.01); *B01J 38/16* (2013.01); B01J 23/24 (2013.01); B01J 23/40 (2013.01); C07C 2521/04 (2013.01); C07C 2521/06 (2013.01); C07C 2521/08 (2013.01); C07C 2521/10 (2013.01); C07C 2523/06 (2013.01); C07C 2523/14 (2013.01); C07C 2523/24 (2013.01); C07C 2523/74 (2013.01)

(58) Field of Classification Search
USPC .................. 585/659, 660, 661, 654, 658, 646
See application file for complete search history.

(56) References Cited

U.S. PATENT DOCUMENTS

| 4,169,815 | A | * | 10/1979 | Drehman ...................... 585/660 |
| 4,229,609 | A | | 10/1980 | Hutson, Jr. et al. |
| 4,973,779 | A | | 11/1990 | Imai et al. |
| 5,151,401 | A | | 9/1992 | Schubert et al. |
| 5,235,121 | A | | 8/1993 | Brinkmeyer et al. |
| 6,670,303 | B1 | | 12/2003 | Heineke et al. |
| 2006/0122448 | A1 | | 6/2006 | Thiagarajan et al. |
| 2007/0142689 | A1 | * | 6/2007 | Hechler et al. ................ 585/660 |

FOREIGN PATENT DOCUMENTS

| DE | 35 26 533 A1 | 2/1986 |
| DE | 198 58 747 A1 | 6/2000 |
| DE | 199 37 107 A1 | 2/2001 |
| DE | 10 2005 061 626 A1 | 6/2007 |
| EP | 0 568 303 A2 | 11/1993 |
| GB | 2 162 082 A | 1/1986 |
| WO | WO 96/33150 A1 | 10/1996 |
| WO | WO 2004/039920 A2 | 5/2004 |

* cited by examiner

*Primary Examiner* — In Suk Bullock
*Assistant Examiner* — Sharon Pregler
(74) *Attorney, Agent, or Firm* — Lathrop & Gage LLP

(57) ABSTRACT

The invention relates to a method for dehydrating alkanes, wherein the alkane is guided in a reactor for the dehydrogenation of alkanes via a catalyst, and the process may be carried out adiabatically or non-adiabatically, and the catalyst for dehydration can be regenerated after the reaction phase by means of transferring a gas, wherein said gas is guided via the catalyst after a short rinsing phase using water vapor, and said regeneration gas consists of a gas containing oxygen and of steam, and after regeneration the catalyst is freed of the gas containing oxygen by transferring steam, wherein the duration of the transfer of a gas containing oxygen is significantly reduced as compared to common methods and represents 70% or less of the total regeneration time, and the catalyst has an increased selectivity for forming alkene by means of carrying out the regeneration at a constant activity, and the catalyst is comprised of a metal of the group of platinum metals or group VIB of the periodic table of the elements, which is applied to a carrier in form of a compound or in elementary form, which substantially consists of oxides of the elements of tin, zinc, or aluminum.

22 Claims, No Drawings

REGENERATION OF CATALYSTS FOR DEHYDRATING ALKANES

BACKGROUND OF THE INVENTION

The catalytic dehydrogenation of hydrocarbons according to the formula $$C_nH_{2n+2} \leftrightarrow C_nH_{2n} + H_2, \quad (1)$$

which is normally performed in the gas phase at a temperature of 450° C. to 820° C., is a highly endothermic equilibrium reaction, the reaction rate of which is limited thermodynamically and which depends on the respective partial pressures and temperature. The dehydrogenation reaction is favoured by low partial pressures of the hydrocarbons and by high temperatures.

The dehydrogenation reaction can be performed adiabatically or non-adiabatically or approximately isothermally. If the dehydrogenation is performed in an adiabatically operated catalyst bed, the endothermic reaction will cause the temperature to decrease over the length of the catalyst bed. The reaction rate in the catalyst bed is thus limited so that several catalyst beds are required to achieve the desired high reaction rates and re-heating is necessary downstream of each catalyst bed. In order to achieve reasonable reaction rates, several catalyst beds are normally arranged in series and the reaction system is re-heated downstream of each catalyst bed.

If the dehydrogenation is performed in a non-adiabatically operated catalyst bed, the catalyst bed can be heated in order to maintain a high temperature. Because of the fact that the temperature in the reaction system is kept constant, the reaction rates are appropriately high. Because of the location of the point of thermodynamic equilibrium, however, the disadvantage is that these high reaction rates can only be achieved at high temperatures, as a result of which the selectivity of olefin formation is reduced. Hence, consecutive reactions will increasingly take place, so that undesired products will form, such as $CH_4$, $CO$, $CO_2$, $C_2H_4$, $C_2H_6$ and coke.

The by-products thus formed, especially finely dispersed coke, precipitate in the course of the reaction on the catalyst, thus causing its state to change continually. The catalyst becomes coated with an undesired substance and is thus less accessible for the reactants. This means that the catalyst becomes deactivated. The activity of the catalyst for alkane dehydrogenation and the selectivity for alkene formation could deteriorate. This would result in deterioration of the efficiency of the process as a whole. Because of operational requirements, such a deactivation can only be tolerated up to certain limit, because an economically viable operation of the plant could no longer be guaranteed. In order, therefore, to counter-act a negative influence on the process, the catalyst has to be regenerated after a certain reaction period in order to recover its activity.

Depending on its characteristics, the catalyst is regenerated by bringing it in contact with an oxygen-bearing gas under conditions defined for the regeneration of the catalyst. The conditions for such a regeneration may differ from those required for the dehydrogenation. An oxygen-bearing gas diluted with steam is also often fed through the catalyst. As a result of this procedure, the by-products on the catalyst are reduced, with the result that the catalyst can regain its activity. If an oxygen-bearing gas diluted with steam is used for catalyst regeneration, the carbon-bearing deposit reacts to carbon dioxide as the main product. The carbon-bearing deposit is converted to gaseous products by this reaction and is removed from the system.

As the conditions for the alkane dehydrogenation process differ from the catalyst regeneration process, the alkane dehydrogenation process is interrupted after a certain period of operation and substituted by the catalyst regeneration process. Thereafter, the reactor bed is again available for dehydrogenation. Both these processes, i.e. the alkane dehydrogenation and catalyst regeneration, are thus performed periodically. In order to render the overall process economically efficient, this can take place in two or a plurality of catalyst beds, in which the reaction and regeneration processes are implemented in cyclic alternation. In order to ensure optimum catalyst regeneration, an optimum production and regeneration sequence should be adopted.

To optimise the plant, a plurality of catalyst lines is used, the dehydrogenation and regeneration processes being performed in cyclic alternation. Some of the catalyst lines can be used for alkane dehydrogenation, while other catalyst lines can simultaneously be regenerated by passing an oxygen-bearing gas or an oxygen-bearing gas diluted with steam over the catalyst. It is also possible to remove the catalyst deposits by a reductive process, although an oxidative process is normally faster and more effective. If a catalyst line has already completed the regeneration process before another catalyst line is ready for regeneration, it can be kept ready for use by continuing to pass an oxygen-free gas through the catalyst bed, thus ensuring that there is always a reaction line is always available.

Examples of such processes can be found in patent literature. DE 19858747 A1 describes a process for catalytic dehydrogenation of alkanes by non-adiabatically operated process. To prolong the dehydrogenation period, water vapour and hydrogen are admixed to the process gas. The dilution of the reaction mixture by these companion gases results in longer service lives of the catalyst, because the separated carbon-bearing deposits partially react with the companion gases to carbon monoxide and water and are removed from the process. After a certain reaction period, the catalyst is completely regenerated by interrupting the dehydrogenation and passing an oxygen-bearing gas through the catalyst bed. In a subsequent purging step after regeneration, hydrogen or a mixture of hydrogen and alkanes are fed through the catalyst bed for a reductive purification of the catalyst surface. These processes can be performed cyclically over several reactor lines.

U.S. Pat. No. 5,235,121 A describes a process for the catalytic dehydrogenation of alkanes in a non-adiabatic process. To regenerate the catalyst, an oxygen-bearing gas diluted with steam is used. In order to reduce heat losses, part of the gas used for regeneration and which is heated in said process is returned to dehydrogenation process. In a purging step following the regeneration, a hydrogen-rich reforming product is fed through the catalyst bed. These processes can be performed in cyclic alternation over a plurality of reactor lines. Preferred starting materials are alkanes with a C number of up to $C_{12}$.

U.S. Pat. No. 4,229,609 A describes a process for the catalytic dehydrogenation of alkanes by a non-adiabatically operated process. To regenerate the catalyst, a consecutive sequence of purge gases is fed through the catalyst bed. The catalyst is first freed from alkane by feeding water-vapour-bearing gas through the catalyst, then regenerated by feeding oxygen-bearing gas through the bed and finally freed from oxygen-bearing regeneration gas by feeding water vapour through the bed. Admittedly, no durations are quoted for the individual regeneration phases. However, an experimental example (column 3) demonstrates the performance of a 30-minute dehydrogenation reaction, followed by a regeneration phase by a 1-minute purge with steam, a 28-minute phase during which an oxygen-bearing gas is fed through the catalyst and finally a 1-minute purge process using steam. The dehydrogenation and catalyst regeneration processes can be performed in cyclic alternation over several reactor lines. Preferred starting materials are alkanes with a C number of $C_6$ to $C_9$.

Irrespective of the mode of operation selected, it is found that that, despite regeneration, the catalyst deteriorates in the course of time with regard to the catalytic dehydrogenation reaction. Regeneration frequently takes place under conditions which adversely affect the catalyst properties. Thus, an oxygen-bearing gas is passed through the catalyst at an elevated temperature, as a result of which the catalyst properties may change. Due to the exothermal burn-off process, temperature control of the catalyst is not always a simple matter. The catalyst could therefore cake and its activity could deteriorate after a few cycles. The selectivity for the desired process of olefin formation could then be reduced.

The aim of the present invention is, therefore, to find regeneration conditions, under which the activity of the catalyst and the selectivity for the desired process of dehydrogenation is maintained even after a large number of regeneration cycles. The sought-after procedure should ideally influence catalyst activity and selectivity in a manner that will permit these parameters to be adapted optimally for the process. The regeneration process should maintain the catalyst activity at a constant level over as many cycles as possible and suppress the formation of carbon-bearing deposits.

Now, it was found that the task can achieved if the catalyst is regenerated by feeding oxygen-free and oxygen-bearing gases are fed through the catalyst bed in a certain temporal ratio. As a result of the mode of operation according to the invention, the activity of the catalyst for the conversion of alkanes is adjusted to a value suitable for the process. The selectivity for the desired dehydrogenation process is not only maintained by the mode of operation according to the invention, but also optimised to continually obtain, in total, a high yield of the desired alkene and to suppress the formation of by-products. In the regeneration process according to the invention, it is possible, to a large extent, to adjust the dehydrogenation equilibrium after feeding the regeneration gas through the catalyst bed even over many regeneration cycles. Thus, an improved mode of operation of the plant under economic aspects can, on the whole, be achieved.

BRIEF SUMMARY OF THE INVENTION

The invention achieves the aim by a process, in which
a mixture containing hydrocarbons, especially alkanes, and which may contain water vapour while being essentially free of oxygen, is continuously fed through a catalyst bed which features the usual dehydrogenation conditions,
the process being characterised in that,
following a production phase of dehydrogenation of several hours' duration, the dehydrogenation reaction is immediately followed by a short phase of feeding an oxygen-free gas stream through the reactor bed for the purpose of purging and removing the reaction gas from the reactor bed, and
this being followed by a phase in which an oxygen-bearing reaction gas is fed through the bed for the purpose of removing any deposits from the catalyst, and
this being followed by a phase in which an oxygen-free gas is fed through the bed for the purpose of purging and removing the regeneration gas from the reactor,
the duration of feeding an oxygen-bearing gas during catalyst regeneration being 70% of the total duration of regeneration or shorter.

DETAILED DESCRIPTION OF THE INVENTION

In an embodiment of the invention, the duration of catalyst regeneration by feeding an oxygen-bearing gas through the catalyst is preferably 20% to 70% of the total duration of regeneration. It is prerequisite for achieving the effect according to the invention that the carbon-bearing deposits on the catalyst are removed through regeneration as completely as possible.

The process according to the invention is particularly suitable for regenerating various different dehydrogenation catalysts. The catalysts should have an adequate activity and selectivity for the desired process of alkane dehydrogenation. In addition, the catalysts should withstand the process of oxidative coke combustion without any adverse effects and should also be well suited for regeneration in order to achieve long service lives. Depending on the applied dehydrogenation process, it is expedient to select a catalyst that is optimally suited for the applied process. A selection of different dehydrogenation processes and the catalysts used therefor are contained in the publication by F. Buonomo, D. Sonfillipo, F. Trifirò, Handbook of Heterogeneous Catalysis, 1$^{st}$ Edition, VCH, Weinheim, 1997 p. 2140 ff. and the literature cited therein.

U.S. Pat. No. 5,151,401 A describes a catalytic system with a high catalytic activity and good selectivity for dehydrogenation reactions. The catalyst is deposited on a carrier material in order to ensure easy handling of the system. The carrier material is produced by calcining a mixture of stannic oxide, zinc oxide and aluminium oxide. In a subsequent step, the catalytically active material, consisting of a chlorinated platinum compound, is deposited on the carrier material. In a washing and drying process, the catalyst is then freed from chlorine which could act corrosively in the applied process. To achieve optimum handling properties, the carrier material can be in the form of pellets, tablets or extrudates. The catalyst deposited on a carrier material can contain additives for improving stability. These additives can be long-chain carboxylic acid salts or calcium aluminates.

U.S. Pat. No. 4,973,779 A describes a further catalytic system with a high catalytic activity and good selectivity for dehydrogenation reactions. The carrier material consists of calcined γ-aluminium oxide into which a tin compound in the form of an oxide, halide, sulphide or the like is dispersed. In a subsequent step, a chlorinated platinum compound and a chlorinated iridium compound is deposited on the carrier material as the catalytically active material. To improve the catalytic activity, the carrier material is provided prior to calcining with an alkali metal salt or preferably with a lithium salt.

DE 3526533 A1 describes a further catalytic system with a high catalytic activity and good selectivity for the dehydrogenation of $C_3$-$C_5$ alkanes. The carrier material consists of η-aluminium oxide which is sprayed with an aqueous solution of chromium(VI) oxide and then dried. During the drying process, chromium oxides are formed from the chromium salt solution, these chromium oxides being finely dispersed in the carrier material and responsible for the actual catalytic activity.

All the catalysts cited above or in the patents mentioned are well suited for regeneration by the process according to the present invention and produce the results according to the invention.

Depending on the catalyst used, various different configurations of the process according to the invention may be selected. One embodiment of the invention provides for the process gas being adiabatically fed through the catalyst bed, the process gas being subjected to a heating process prior to being fed through the catalyst bed.

In a further embodiment of the invention, the process takes place non-adiabatically. As the dehydrogenation reaction proceeds endothermically, heat has to added for this purpose and the catalyst bed must be heated.

It is also possible to overcome the thermodynamic limitation of the dehydrogenation step by subjecting part of the hydrogen obtained during dehydrogenation in accordance with $$2H_2 + O_2 \rightarrow 2H_2O \qquad (2)$$

to selective combustion. This is also known as SHC which stands for "Selective Hydrogen Combustion". In view of the fact that hydrogen is used up in this reaction, the dehydrogenation equilibrium is shifted towards higher yields, i.e. towards olefin formation. In addition, heat is generated in the selective combustion of hydrogen, as a result of which the reaction mixture containing unconverted alkane is heated. The processes of endothermic dehydrogenation of alkanes and exothermal selective hydrogen combustion can thus be combined, so that the process proceeds virtually autothermally.

To facilitate process control, the process steps of dehydrogenation and oxidative combustion of the hydrogen obtained, are frequently performed successively. The reaction gas is first fed through a catalyst bed for dehydrogenation. After dehydrogenation, oxygen-bearing gas is added to the process gas. In the next process step, selective hydrogen combustion (SHC) (2), the reaction gas is heated. As a result, the product gas can be fed to another dehydrogenation step, appropriately less heat being required for this process step.

WO 2004/039920 A2 describes, by way of an example, a process for the catalytic dehydrogenation of hydrocarbons with subsequent oxidation of the hydrogen obtained in the dehydrogenation process step. In a first process step, an alkane-bearing gas mixture is fed through a catalyst bed, which is designed for alkane dehydrogenation (1) and which contains a tin- and platinum-bearing catalyst which is deposited on a carrier material of aluminate. After the dehydrogenation process step, the hydrogen- and alkane-bearing product gas is mixed with an oxygen- and water-vapour-bearing gas and fed through a second catalyst bed, which is designed for hydrogen combustion (2). The characteristic feature of this process is that the same catalyst is used for the dehydrogenation (1) process step and for the oxidative hydrogen combustion (2) process step. The combustion of hydrogen heats the reaction mixture and simultaneously removes the hydrogen from the product gas stream. As a result, the equilibrium of the reaction for dehydrogenating alkanes shifts towards olefin side. After hydrogen oxidation, the product mixture is subjected to further dehydrogenation, the product mixture being either returned to the reactor of the first step or fed to a separate dehydrogenation reactor.

The combination of alkane dehydrogenation with a process step of selective hydrogen combustion (SHC) (2) is well suited for performing the process according to the present invention, in order to ensure that the energy consumption of the process is reduced and the process proceeds with high yields.

For the oxidative hydrogen combustion (2) it is possible to use a catalyst that is suitable both for the dehydrogenation of alkanes and for the oxidative combustion of hydrogen. For the oxidative hydrogen combustion, another catalyst is also suitable, which selectively oxidises hydrogen, such as is used in WO 96/33150 A1.

It is important for the process according to the present invention that the duration of the regeneration phase and of the subsequent purge phase is set so as to ensure that the activity of the dehydrogenation catalyst is maintained even after numerous regeneration cycles and the selectivity for the dehydrogenation process can be optimally adjusted. Thanks to the mode of operation according to the invention, a virtually complete alkane dehydrogenation equilibrium can be set after each regeneration phase and the formation of by-products can be minimised.

In an embodiment of the invention, the alkane is mixed with steam prior to dehydrogenation and, consequently, diluted. The percentage molar steam/alkane ratio may, in an embodiment of the invention, range from 1 to 99. For further optimisation of the reaction, the molar steam/alkane ratio can range between 1 and 10, the ideal range being 2 to 6.

In a further embodiment of the invention, the oxygen-bearing gas of the regeneration phase is diluted with steam. If steam is chosen as the companion gas for the oxygen-bearing gas, the molar gas/steam ratio is preferably 0.01 mole percent to 50 mole percent oxygen to 99.99 to 50 mole percent steam. To further optimise the reaction, the molar oxygen/steam ratio can amount to 0.05 to 35 mole percent oxygen to 99.95 to 65 mole percent steam, ideally 0.5 to 25 mole percent oxygen to 99.5 to 75 mole percent steam.

In a further embodiment of the present invention, the oxygen-bearing gas of the regeneration phase is diluted with nitrogen or a noble gas or another inert gas. If nitrogen or an inert gas is chosen as the companion gas for the oxygen-bearing gas, the percentage molar ratio of oxygen to nitrogen or the inert gas preferably amounts to 0.01 to 50 mole percent oxygen to 99.99 to 50 mole percent nitrogen or inert gas. To further optimise the reaction, the molar ratio of oxygen to nitrogen or the inert gas can amount to 0.05 to 35 mole percent oxygen to 99.95 to 65 mole percent nitrogen or inert gas and ideally 0.5 to 25 mole percent oxygen to 99.5 to 75 mole percent nitrogen or inert gas.

Alkanes with a C number in the range of $C_2$ to $C_{20}$ can be used as the starting material for the alkane dehydrogenation process according to the present invention. An embodiment of the invention provides for the use of ethane or propane or butane or a mixture of these gases as the starting material. The process according to the invention is particularly suitable for the production of ethene or propene or butenes or a mixture of these gases.

The process uses a catalyst which is characterised in that it is suitable for the dehydrogenation of alkanes in the process according to the invention. As a rule, such catalysts contain a metal from group VIIIB of the periodic table of the elements. To improve its handling properties, the catalytically active material can be deposited on a carrier material consisting of oxides of the elements aluminium, silicon, magnesium, zirconium, zinc or tin. A catalyst, such as is described in U.S. Pat. No. 5,151,401 A, can be used particularly advantageously as the catalyst for the process according to the present invention. However, any other catalyst that is suitable for the dehydrogenation of alkanes may also be used. Such catalysts are, for example, those that contain metals from group VIB of the periodic table of the elements. To improve its handling properties, the catalytically active material may be deposited on a carrier material consisting of oxides of the elements aluminium, silicon or magnesium.

The process according to the present invention is run under a pressure such as is used for alkane dehydrogenation under normal conditions. Typical pressures are 0.1 to 15 bar. This pressure can be maintained for catalyst regeneration.

The temperature range selected for running the dehydrogenation reaction for the process according to the present invention is such as is used for the dehydrogenation of alkanes under normal conditions. Typical temperatures are 450° C. to 820° C. Temperatures of 450° C. to 750° C. are normally selected for regeneration. If the mode of operation is non-adiabatic, the heating of the catalyst bed may cause the regeneration gas temperature to increase during regeneration.

An embodiment of the invention provides for the dehydrogenation (1) to be performed in a first reaction step non-adiabatically and for admixing a gas to the product mixture from the first reaction step for cooling purposes. This gas consists preferably of oxygen and water vapour. If further cooling of the reaction gas is required, liquid water may be admixed to the reaction gas. The cooled reaction gas may then be fed to a second process step for the purpose of oxidative hydrogen combustion (2).

In a further embodiment of the present invention, a third process step of further alkane dehydrogenation follows the process step of oxidative hydrogen combustion. For this purpose, the process gas has to be heated either directly or indirectly by an oven.

The process according to the present invention is characterised by its simplicity and high effectiveness. As a result of the catalyst regeneration process described, the selectivity of conversion from alkane to alkene can not only be maintained over many regeneration cycles but even improved without any loss of activity. All in all, a higher yield of desired alkene is achieved. From the economic point of view, a marked overall improvement of the mode of operation of the plant is thus achieved.

The process according to the present invention is described below by means of some examples of its implementation without being limited to these examples. The examples are merely typical variants of the process.

A model reactor, such as is typically used for testing dehydrogenation reactions, was used for the experimental examples. The model reactor consists of a metal tube which can be heated and which is filled with the catalyst. The metal tube is positioned vertically and provided at its upper end with an inlet device for feeding the mixture to be dehydrogenated through the catalyst bed. The inlet device is provided with a heating device in order to be able to feed solid hydrocarbons through the reactor even at room temperatures. Devices are arranged at the inlet and outlet ends of the reactor, which permit the pressure and temperature of the gas being fed through the reactor to be measured and adjusted. A four-way valve is provided to stop the hydrocarbon feed and to replace it by an oxygen-bearing regeneration gas or a purge gas. A further independent inlet device is provided to admix a dilution gas to the gas stream. The reaction products are collected at the outlet end of the reactor. A device is located there for gas-chromatographic measurements for analysing the reaction product. The results displayed are molar concentrations which can be converted to percentage reaction yields and selectivities.

The invention is illustrated on the basis of several experiments. Propane is mixed with water vapour and fed into the reactor via the inlet device. The precise reaction conditions are shown in table 1.

TABLE 1

| Reactor inlet temperature in dehydrogenation and regeneration modes | 510° C. |
| Reactor outlet temperature in dehydrogenation mode | 552° C. |
| Reactor outlet temperature in regeneration mode | 615° C. |
| Propane gas flow (LHSV) | 15 h$^{-1}$ |

TABLE 1-continued

| Pressure | 6.6 bar |
| Molar ratio of water vapour to propane | 3.5 |

In a first experiment with three examples, propane was dehydrogenated over 7 hours. This was followed by a purge phase with water vapour of 5 minutes' duration, a regeneration phase with an oxygen-bearing and water-vapour-bearing gas, and a further purge phase with water vapour of varying duration. In further dehydrogenation period, the conversion of propane and the selectivity to propene were measured (table 2).

EXAMPLE 1

Comparison Example

EXAMPLE 2

Inventive Example

EXAMPLE 3

Counter-Example

TABLE 2

| Example | Dehydrogenation phase | Regeneration phase I[1] | Purge phase II[2] | Propane conversion | Propene selectivity |
|---|---|---|---|---|---|
| 1 (comparison example) | 7 h | 50 min. | 5 min. | 19.4% | 95.7% |
| 2 (inventive example) | 7 h | 20 min. | 35 min. | 19.2% | 96.4% |
| 3 (counter-example) | 7 h | 10 min. | 45 min. | 16.2% | 97.2% |

[1] Preceded by a 5-minute purge phase with water vapour, the regeneration gas consists of air/water vapour with a total of 2 percent by volume oxygen
[2] Purge gas consists of water vapour The selectivity for the olefin formation at virtually identical conversion rate is highest in the inventive example and the inventive counter-example. The counter-example with prolonged purge phase demonstrates a decreasing catalyst activity.

In a further experiment (table 3), an alkane dehydrogenation was performed without catalyst regeneration close to the thermodynamic equilibrium. The product gas was sampled after 280 minutes, 510 minutes and 740 minutes. The conversion rate was virtually identical whereas the selectivity increases markedly.

TABLE 3

| | Dehydrogenation time: Conversion/selectivity | Dehydrogenation time: Conversion/selectivity | Dehydrogenation time: Conversion/selectivity |
|---|---|---|---|
| Example 4 | 280 minutes: 19.2%/96.8% | 510 minutes: 19.0%/97.1% | 740 minutes: 18.9%/97.4% |

In a further experiment (table 4), propane was dehydrogenated, the catalyst was regenerated without any oxygen feed and the propane was again dehydrogenated. The activity of the catalyst is reduced markedly as a result of the lesser coke removal.

TABLE 4

| | Dehydrogenation time: Conversion/selectivity | Purge time[2]: Conversion/ selectivity | Dehydrogenation time: Conversion/selectivity |
|---|---|---|---|
| Example 5 | 7 h: 20.0%/95.4%[1] | 60 minutes | 7 h: 13.4%/96.9%[1] |

[1]Measured after 280 min.,
[2]Regeneration with oxygen-free gas

The invention claimed is:

1. A process for the dehydrogenation of alkanes, in which a mixture containing an alkane, which may contain water vapour and which contains essentially no oxygen, is fed continuously through a catalyst bed which features standard dehydrogenation conditions, comprising
   dehydrogenating the alkane in a production phase of seven hours which is immediately followed by a phase during which an oxygen-free gas is fed through the reactor bed for the purpose of purging and expelling the reaction gas from the reactor bed,
   followed by feeding an oxygen-bearing regeneration gas through the catalyst bed for the purpose of removing from the catalyst any deposits formed during the dehydrogenation reaction, and
   followed by feeding an oxygen-free gas through the reactor for the purpose of purging and expelling the regeneration gas from the reactor,
   wherein the duration of feeding the oxygen-bearing gas through the reactor for catalyst regeneration is 70% of the total duration of regeneration or less,
   the entire regeneration duration amounts to one hour.

2. The process according to claim 1, wherein the duration of catalyst regeneration by feeding the oxygen-bearing gas through the reactor amounts to 20% to 70% of the total duration of regeneration.

3. The process according to claim 1, wherein the oxygen-bearing regeneration gas is diluted with steam.

4. The process according to claim 1, wherein the oxygen-bearing regeneration gas is diluted with nitrogen or an inert gas.

5. The process according to claim 3, wherein the molar oxygen/steam ratio selected for the mixture of oxygen-bearing gas and steam for regeneration amounts to 0.05 to 50 mole percent oxygen to 99.95 to 50 mole percent steam.

6. The process according to claim 3, wherein the molar ratio of oxygen to nitrogen or an inert gas selected for the mixture of oxygen-bearing gas and nitrogen or inert gas for regeneration amounts to 0.05 to 50 mole percent oxygen to 99.95 to 50 mole percent nitrogen or inert gas.

7. The process according to claim 1, wherein, the oxygen-bearing gas comprises atmospheric air, wherein the quantity of air being such as to feed 0.05 to 50 mole percent oxygen to 99.95 to 50 mole percent nitrogen or inert gas through the reactor.

8. The process according to claim 1, wherein the starting material used for alkane dehydrogenation consists of alkanes with a C number in the range of $C_2$ to $C_{20}$.

9. The process according to claim 1, wherein the catalyst used for the process according to the invention contains a metal from group VIIIB of the periodic table of the elements.

10. The process according to claim 1, wherein the catalyst used for the process according to the invention contains a metal from group VIB of the periodic table of the elements.

11. The process according to claim 1, wherein the catalyst is deposited on a carrier material consisting of oxides of the elements aluminium, silicon, magnesium, zirconium, zinc or tin or mixtures of these element oxides.

12. The process according to claim 1, wherein the molar steam/alkane ratio in dehydrogenation amounts to 1 to 99 mole percent.

13. The process according to claim 1, wherein the dehydrogenation process step is performed non-adiabatically.

14. The process according to claim 1, wherein the dehydrogenation process step proceeds in an oven which can heat the process gas to a temperature in the range of 450° C. to 820° C.

15. The process according to claim 1, wherein the dehydrogenation process step is performed adiabatically.

16. The process according to claim 1, wherein the catalyst regeneration process step proceeds at a temperature of 450° C. to 750° C.

17. The process according to claim 1, wherein the pressure selected for dehydrogenation and regeneration is 0.1 bar to 15 bar.

18. The process according to claim 1, wherein the dehydrogenation is performed in a first reaction step non-adiabatically yielding a product mixture and in a first process step that a gas containing liquid water or water vapour and oxygen is subsequently admixed to the product mixture, consisting of alkanes, alkenes, water vapour, hydrogen and by-products, from this first reaction step yielding a reaction mixture, and that the reaction mixture thus obtained is continuously fed through a further catalyst bed in a second process step for oxidising the hydrogen and further dehydrogenation of hydrocarbons.

19. The process according to claim 18, wherein an additional oxygen-bearing gas is subsequently admixed to the reaction mixture obtained from the first process step resulting in a second reaction mixture and that the resulting second reaction mixture is fed continuously through a further catalyst bed in a second process step for oxidising the hydrogen and that the mixture is then fed through a further catalyst bed in at least a third process step for alkane dehydrogenation.

20. The process according to claim 1, wherein an oxygen-bearing gas is subsequently admixed to the reaction mixture obtained from the first process step and that the resulting reaction mixture is fed continuously through a further catalyst bed in a second process step for oxidising the hydrogen and that the mixture is then returned to the first catalyst bed for alkane dehydrogenation.

21. The process according to claim 1, wherein any commonly used dehydrogenation catalyst can be employed for the catalyst bed in the first process step and that the dehydrogenation catalyst used for the second or any further process steps is a catalyst which not only features a good dehydrogenation activity but also a good activity for selective hydrogen oxidation or only for selective hydrogen oxidation.

22. A process for the dehydrogenation of alkanes, in which a mixture containing an alkane, which may contain water vapour and which contains essentially no oxygen, is fed continuously through a catalyst bed which features standard dehydrogenation conditions, comprising
   dehydrogenating the alkane in a production phase of seven hours which is immediately followed by a phase during which an oxygen-free gas is fed through the reactor bed for the purpose of purging and expelling the reaction gas from the reactor bed,
   followed by feeding an oxygen-bearing regeneration gas through the catalyst bed for the purpose of removing from the catalyst any deposits formed during the dehydrogenation reaction, and
   followed by feeding an oxygen-free gas through the reactor for the purpose of purging and expelling the regeneration gas from the reactor, wherein the duration of feeding the oxygen-bearing gas through the reactor for catalyst regeneration is 70% of the total duration of regeneration or less, the entire regeneration duration amounts to one hour, the catalyst used for the process according to the invention contains a metal from group VIB or group VIIIB of the periodic table of the elements, and the catalyst is deposited on a carrier material consisting of oxides of the elements aluminium, silicon, magnesium, zirconium, zinc or tin or mixtures of these element oxides.

* * * * *